(12) United States Patent
Baohua et al.

(10) Patent No.: US 8,334,109 B2
(45) Date of Patent: *Dec. 18, 2012

(54) REAGENT FOR BLOOD ANALYSIS AND METHOD OF USING THE SAME

(75) Inventors: Zhang Baohua, Shenzhen (CN); Xu Bing, Shenzhen (CN); Kuang Yuji, Shenzhen (CN); Lei Ting, Shenzhen (CN); Shao Jianhui, Shenzhen (CN); Bao Dequan, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 397 days.

This patent is subject to a terminal disclaimer.

(21) Appl. No.: 12/633,452

(22) Filed: Dec. 8, 2009

(65) Prior Publication Data
US 2010/0143955 A1 Jun. 10, 2010

(30) Foreign Application Priority Data
Dec. 8, 2008 (CN) .......................... 2008 1 0218267

(51) Int. Cl.
C07D 403/08 (2006.01)
C12Q 1/68 (2006.01)
G01N 1/30 (2006.01)

(52) U.S. Cl. ............ 435/14; 435/29; 514/400; 514/408; 514/415; 514/452; 548/455

(58) Field of Classification Search .................... 435/14, 435/29; 514/400, 408, 415, 452
See application file for complete search history.

(56) References Cited

U.S. PATENT DOCUMENTS

| | | | |
|---|---|---|---|
| 4,882,284 A | 11/1989 | Kirchanski et al. |
| 5,155,044 A | 10/1992 | Ledis et al. |
| 5,196,346 A | 3/1993 | Lefevre et al. |
| 5,264,369 A | 11/1993 | Sakata et al. |
| 5,298,426 A | 3/1994 | Inami et al. |
| 5,308,772 A | 5/1994 | Sakata et al. |
| 5,413,938 A | 5/1995 | Tsujino et al. |
| 5,516,695 A | 5/1996 | Kim et al. |
| 5,518,928 A | 5/1996 | Cremins et al. |
| 5,538,893 A | 7/1996 | Sakata et al. |
| 5,559,037 A | 9/1996 | Kim et al. |
| 5,618,733 A | 4/1997 | Sakata et al. |
| 5,648,225 A | 7/1997 | Kim et al. |
| 5,677,183 A | 10/1997 | Takarada et al. |
| 5,681,733 A | 10/1997 | Su et al. |
| 5,874,310 A | 2/1999 | Li et al. |
| 5,879,900 A | 3/1999 | Kim et al. |
| 5,917,584 A | 6/1999 | Li et al. |
| 5,958,776 A | 9/1999 | Sakata et al. |
| 6,197,851 B1 | 3/2001 | Maxwell et al. |
| 6,214,625 B1 | 4/2001 | Li et al. |
| 6,368,864 B1 | 4/2002 | Deka et al. |
| 6,410,330 B1 | 6/2002 | Li et al. |
| 6,472,215 B1 | 10/2002 | Huo et al. |
| 6,551,831 B2 | 4/2003 | Gupta et al. |
| 6,573,102 B2 | 6/2003 | Li et al. |
| 6,664,100 B2 | 12/2003 | Reverso |
| 6,673,618 B1 | 1/2004 | Li et al. |
| 6,911,313 B2 | 6/2005 | Houwen et al. |
| 6,916,658 B2 | 7/2005 | Li et al. |
| 7,008,792 B2 | 3/2006 | Lopez et al. |
| 7,049,093 B2 | 5/2006 | Tsuji et al. |
| 7,208,319 B2 | 4/2007 | Lopez et al. |
| 2002/0022004 A1 | 2/2002 | Licha et al. |
| 2003/0219580 A1 | 11/2003 | Tagge et al. |
| 2004/0241770 A1 | 12/2004 | Houwen et al. |
| 2005/0208534 A1 | 9/2005 | Dallwig et al. |
| 2006/0275801 A1 | 12/2006 | Henkin et al. |
| 2006/0292658 A1 | 12/2006 | Lynch |
| 2007/0178597 A1 | 8/2007 | Tsuji et al. |

(Continued)

FOREIGN PATENT DOCUMENTS

CN 1364829 8/2002
(Continued)

OTHER PUBLICATIONS

Tatarets, et al., Analytica Chimica Acta, 2006, 570(2), 214-223.*
(Continued)

*Primary Examiner* — Susannah Chung
(74) *Attorney, Agent, or Firm* — Kory D. Christensen; Matthew S. Bethards; Stoel Rives LLP

(57) ABSTRACT

A reagent for blood analysis includes: (1) a compound having the general formula I; and (2) at least one surfactant selected from cationic surfactants and nonionic surfactants. In another aspect a method for differentiating and counting blood cells is provided, the method includes the following steps: (a) mixing a blood sample with the reagent for blood analysis according to the present disclosure to form a cell suspension; (b) detecting scattered light signals and fluorescence signals of cells in the blood sample; and (c) differentiating and counting the cells in the blood sample based upon the scattered light signals and fluorescence signals. The reagent for blood analysis may be effective for identifying and counting erythroblasts and/or basophils in a blood sample to be detected, and meanwhile counting leukocytes therein.

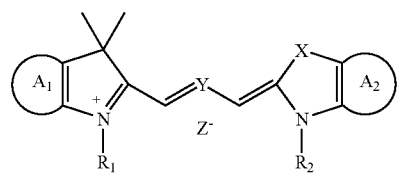

Formula I

23 Claims, 6 Drawing Sheets

U.S. PATENT DOCUMENTS

| | | | |
|---|---|---|---|
| 2007/0203343 | A1 | 8/2007 | West et al. |
| 2007/0287145 | A1 | 12/2007 | Mizukami et al. |
| 2007/0298408 | A1 | 12/2007 | Mizukami et al. |
| 2008/0153170 | A1 | 6/2008 | Garrett et al. |
| 2010/0112584 | A1* | 5/2010 | Shao et al. .................. 435/6 |
| 2011/0136242 | A1 | 6/2011 | Marx et al. |
| 2011/0159483 | A1 | 6/2011 | Zhao et al. |

FOREIGN PATENT DOCUMENTS

| | | |
|---|---|---|
| CN | 1637077 | 12/2004 |
| CN | 1939978 | 9/2005 |
| WO | WO 2005/108405 | 11/2005 |
| WO | WO 2008/040994 | 4/2008 |

OTHER PUBLICATIONS

Ioffe, et al., Journal of Fluorescence (2006), 16(1), 47-52.*
Oswald, et al., Bioconjugate Chem., 1999, 10, 925-931.*
Ioffe, et al., Journal of Fluorescence, 2006, 16(1), pp. 47-52.*
U.S. Appl. No. 12/607,614, filed Oct. 28, 2009, Shao et al.
Chen Xin, Yao Zu-Guang, "Synthesis and Properties of N-Benzylindotricarbocyanine Dyes". Chemical Journal of Chinese Universities, vol. 17, No. 10, 1996, pp. 1613-1616.
Mujumadar et al., "Cyanine Dye Labeling Reagents: Sulfoindocyanine Succinimidyl Esters." Biocojugate Chemistry, vol. 4, No. 2, 1993, pp. 105-111.
Office Action dated Apr. 24, 2012 for U.S. Appl. No. 12/826,231.
Notice of Allowance and Fees Due dated Aug. 1, 2012 for U.S. Appl. No. 12/826,231.
Office Action dated Jul. 23, 2012 for U.S. Appl. No. 12/607,614.
Restriction Requirement dated May 31, 2012 for U.S. Appl. No. 12/607,614.

* cited by examiner

REAGENT FOR BLOOD ANALYSIS AND METHOD OF USING THE SAME

RELATED APPLICATIONS

This application claims priority to Chinese Patent Application No. 200810218267.2, filed Dec. 8, 2008, for "REAGENT FOR BLOOD ANALYSIS AND METHOD OF USING THE SAME," the disclosure of which is fully incorporated herein by reference.

TECHNICAL FIELD

The present disclosure relates to the field of blood analysis, more particularly to the differentiating and counting of cells in the blood.

BRIEF SUMMARY

The present disclosure relates to a reagent for blood analysis and a method of using the same. More particularly, the present disclosure relates to a reagent for blood analysis useful for differentiating and counting cells in the blood and a method of using said reagent to perform blood analysis.

DETAILED DESCRIPTION

Figure 1:
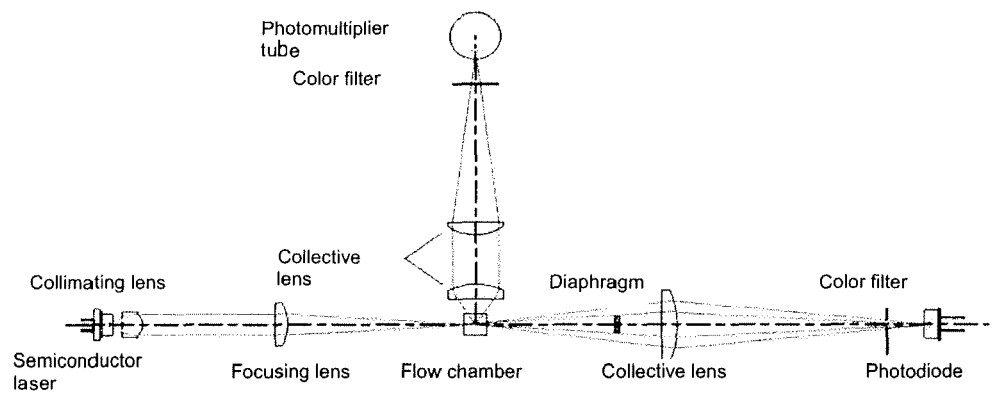
FIG. 1 is a schematic diagram of an exemplary optical system of a flow cytometer used in the analysis method in the examples of the present disclosure.

In normal human bodies, basophils are relatively scarce, accounting for only 0-1% of total leukocytes. However, there is a marked increase in the number of basophils in such disorders as heavy metal intoxication, Hodgkin's disease, and chronic myelocytic leukemia. Therefore, counting basophils is important to the diagnosis of these disorders.

In the past, some chemical dyes were commonly used clinically for staining and counting basophils, including Wright-Giemsa compound stain, toluidine blue stain and neutral red stain, etc. These methods mainly provide the result of a percentage count of basophils and suffer from long operational time and susceptibility to subjectivity of the operator, thus being not suitable for the analysis of large scale clinical samples.

U.S. Pat. No. 4,882,284 discloses a method for differentiating and counting leukocytes. Said method involves staining leukocytes with a fluorescence dye and detecting the fluorescence, side scattered light and forward scattered light signals, via which the leukocytes are differentiated into five subgroups, namely, lymphocytes, monocytes, neutrophils, eosinophils and basophils. However, because the fluorescence and forward scattered light signals of basophils partly overlap with those of neutrophils and monocytes, using such method to detect samples having a normal or relatively low number of basophils will result in inaccurate count and differentiation results.

U.S. Pat. No. 5,196,346 discloses a reagent and a method for counting basophils. The reagent contains, among others, polyoxyethylene ether surfactant. The method only employs a single parameter (impedance signal) to achieve the differentiation and count of basophils such that it has a low accuracy as compared to those multi-parameter methods.

U.S. Pat. Nos. 5,538,893, 5,677,183 and 5,518,928 respectively disclose a reagent and a method for analyzing basophils. The main components of the reagent include polyoxyethylene glycol ether as the nonionic surfactant. Such a reagent can render naked the nuclei of the leukocytes other than basophils and maintain the intactness of basophils alone. The impedance of or the low-angle scattered light from the cells is detected to obtain signals representing cell size, and the side scattered light or high-angle scattered light from the cells is detected to obtain signals representing intracellular structure. By combining these two kinds of signals, the differentiation and count of basophils are achieved.

U.S. Pat. No. 6,214,625 discloses a reagent and a method for differentiating and counting basophils and eosinophils.

The reagent is composed of a hemolytic agent and a stabilizing agent. The hemolytic agent is mixed with blood cells for a period of time to the extent that only the basophils are left structurally intact prior to the addition of the stabilizing agent. Finally, the basophils are differentiated and counted by detecting the impedance of and the rotated light scatter signals of the cells or the radio frequency and the log light scatter signals of the cells. Such a method measures a number of parameters and needs a combination of special detection devices, such that the instrument is structurally complex as well as costly.

The basic principle behind the analysis of basophils by flow cytometry or impedance method is size-based differentiation. The blood sample is generally treated under acidic conditions, under which basophils remain morphologically intact by virtue of their characteristics, while the nuclei of leukocytes other than basophils are substantially rendered naked, so that basophils can be identified by size. However, for some abnormal blood samples that contain immature cells or abnormal cells or the like, as the nuclei of these cells would not be rendered naked under such treatment conditions and as such these cells remain structurally intact, identification of basophils by size will yield a false increase in the number of basophils.

Generally, total leukocyte counting is performed in the channel for identifying basophils. However, due to interference of erythroblasts (or nucleated red blood cells), the total leukocyte count for the samples containing erythroblasts suffers from deviation from the accurate value. Therefore the erythroblast count needs to be separately obtained and deducted in order to acquire an accurate total leukocyte count.

Erythroblasts, as immature erythrocytes, can be classified into early, intermediate and orthochromatic normoblasts. They are normally present in hematopoietic tissues and organs such as bone marrow and are rarely seen in the peripheral blood of normal adults. The occurrence of erythroblasts in the peripheral blood is associated with a variety of disease states and poor prognosis, such as hemolytic anemia, acute and chronic leukemia, erythroleukemia, extramedullary hemopoiesis and severe hypoxia, etc., and is also of clinical importance to the diagnosis and prognosis of some fetal diseases.

Traditionally, detection of erythroblasts in the peripheral blood is performed by manual microscopic examination. This approach is susceptible to the subjectivity of the observer. Moreover, it suffers from a large error due to the small number of cells counted and is time-consuming and labor-intensive as well.

U.S. Pat. Nos. 5,648,225, 5,559,037, 5,874,310, 6,472,215, 5,298,426 and 6,911,313 respectively disclose a method for detecting erythroblasts. In these disclosed methods, separate reagents and channels are needed for identifying basophils and erythroblasts, such that these two types of cells may not be identified simultaneously. In addition, the cost of the reagent and the instrument maybe high, and the operation is complex, which affects the overall test speed of blood analysis.

In one aspect of the present disclosure there is provided a reagent for blood analysis, said reagent comprising:

(1) a compound having the general formula I:

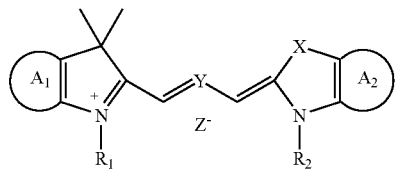

wherein $R_1$ and $R_2$ are each independently selected from at least one of the following: $C_{1-18}$alkylCOOR$_6$, $C_{1-18}$alkylOR$_6$ and benzyl, wherein said benzyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl, provided that $R_1$ and $R_2$ are not all simultaneously benzyl;

$R_6$ in each occurrence is independently H, $C_{1-18}$alkyl or phenyl, wherein said phenyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;

Y is —CH—CH=CH—,

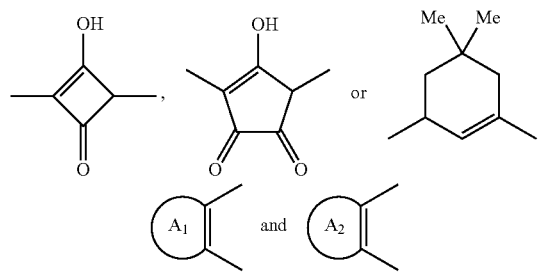

are each independently

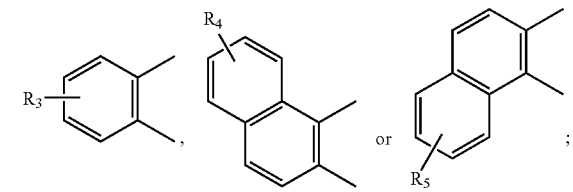

$R_3$, $R_4$ and $R_5$ are each independently selected from at least one of the following: H, halogen, cyano, hydroxyl, $C_{1-18}$alkyl, $C_{1-18}$alkylsulphonyl, sulphonyl and $C_{1-5}$alkyl-COOR$_7$;

$R_7$ is H or $C_{1-6}$alkyl; and $Z^-$ is an anion; and (2) at least one surfactant selected from cationic surfactants and nonionic surfactants.

In one embodiment, when Y is —CH—CH=CH— and

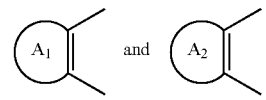

are simultaneously

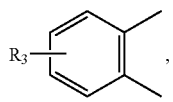

$R_3$ are not simultaneously sulphonyl.

In another aspect of the present disclosure there is provided a kit comprising the reagent for blood analysis according to the present disclosure, wherein said compound having the general formula I and said surfactant(s) are individually stored in separate containers, or alternatively, said compound having the general formula I and said surfactant(s) are formulated as a single solution. Said kit is useful for differentiating and counting blood cells. In some embodiments, said kit is effective for identifying and counting erythroblasts and/or basophils in a blood sample to be detected, and meanwhile counting leukocytes therein.

In yet another aspect of the present disclosure there is provided a method for differentiating and counting blood cells, said method comprising the following steps: (a) mixing a blood sample with the reagent for blood analysis according to the present disclosure to form a cell suspension; (b) detecting scattered light signals and fluorescence signals from cells in the cell suspension; and (c) differentiating and counting the cells in the blood sample based upon the scattered light signals and fluorescence signals.

In still another aspect of the present disclosure there is provided use of the reagent for blood analysis according to the present disclosure in the manufacture of a kit useful for differentiating and counting blood cells.

According to the present disclosure, the identifying and counting of basophils and erythroblasts may be achieved using a single reagent and a single detection channel. Basophils may be counted accurately, while leukocytes may be counted accurately as well without the interference of erythroblasts. The reagent for blood analysis according to the present disclosure can also be used to identify and count basophils or erythroblasts separately.

DEFINITIONS

Unless otherwise specified, the following terms as used herein have the following meanings.

The term "alkyl" as used herein individually or in combination with other groups refers to straight or branched alkyl groups containing 1-18 carbon atoms, such as 1-12, or alternatively 1-8, or 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The same rules apply to other groups as used throughout the present specification.

The term "halogen" as used herein includes fluorine, chlorine, bromine and iodine.

The term "biological sample" as used herein includes, but is not limited to, peptides, proteins, nucleic acids, and erythroblasts in the blood.

The term "aryl" as used herein refers to an aromatic monocyclic group or an aromatic fused 2 or 3 ring group containing 3 to 20 carbon atoms, optionally also containing 1 to 3 heteroatoms selected from N, O and S.

The term "heterocyclyl" as used herein refers to a non-aromatic monocyclic group or a non-aromatic fused 2 or 3 ring group containing 3 to 20 carbon atoms, also containing 1 to 3 heteroatoms, optionally selected from N, O and S.

The term "sulphonyl" as used herein refers to —$SO_3H$ group or —$SO_3^-M$ group, wherein M is a counterion, including e.g., alkali metal ions (such as $K^+$ ion) or alkaline earth metal ions.

The term "alkylsulphonyl" as used herein refers to a group in which the "sulphonyl" as defined above is attached to the remaining moieties of the molecule via the "alkyl" as defined above.

The term "erythroblast" as used herein includes early erythroblast, intermediate erythroblast and late erythroblast.

The Reagent for Blood Analysis According to the Present Disclosure

The reagent and method disclosed in the present disclosure can be used to detect erythroblasts and basophils in whole blood. Following the addition of the reagent for blood analysis according to the present disclosure into the whole blood, the components in the reagent rapidly lyze the erythrocytes while leaving the nuclei of the erythroblasts intact, and at the same time partly lyze the membrane of the leukocytes other than the basophils, such that the cells can be differentiated using the fluorescence scattering method.

In one aspect of the present disclosure there is provided a reagent for blood analysis, said reagent comprising:
(1) a compound having the general formula I:

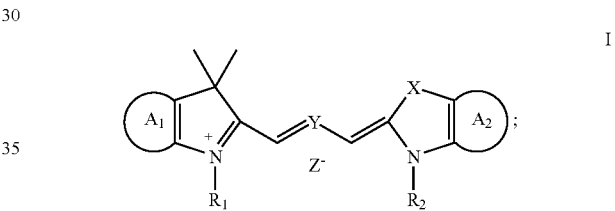

and
(2) at least one surfactant selected from cationic surfactants and nonionic surfactants.

The Compound Having the General Formula I

The compound useful in the present disclosure as a fluorescent dye has the structure of the following general formula I:

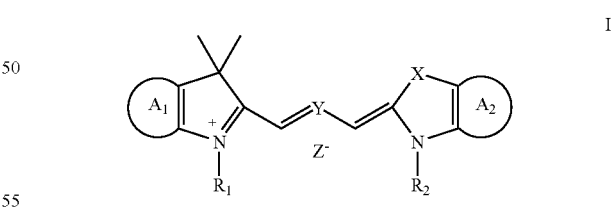

wherein $R_1$ and $R_2$ are each independently selected from at least one of the following: $C_{1-18}$alkylCOOR$_6$, $C_{1-18}$alkylOR$_6$ and benzyl, wherein said benzyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl, provided that $R_1$ and $R_2$ are not all simultaneously benzyl;

$R_6$ in each occurrence is independently H, $C_{1-18}$alkyl or phenyl, wherein said phenyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;

Y is —CH—CH=CH—

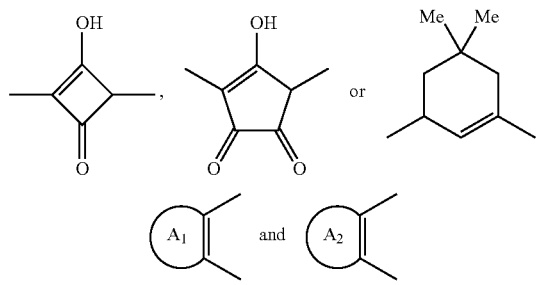

are each independently

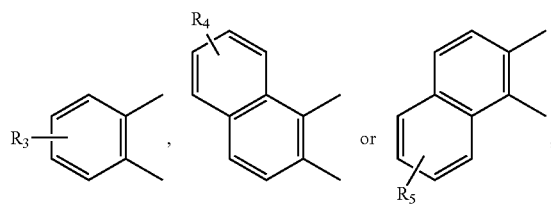

$R_3$, $R_4$ and $R_5$ are each independently selected from at least one of the following: H, halogen, cyano, hydroxyl, $C_{1-18}$alkyl, $C_{1-18}$alkylsulphonyl, sulphonyl and $C_{1-5}$alkyl-$COOR_7$;

$R_7$ is H or $C_{1-6}$alkyl; and $Z^-$ is an anion.

In one embodiment, $R_1$ and $R_2$ are each independently selected from at least one of following: $C_{1-6}$alkylCOOR$_6$, $C_{1-6}$alkylOR$_6$ and benzyl, provided that $R_1$ and $R_2$ are not all simultaneously benzyl.

In one embodiment, $R_6$ in each occurrence is independently H, $C_{1-6}$alkyl or phenyl.

In one embodiment, $R_3$, $R_4$ and $R_5$ are each independently selected from at least one of the following: H, halogen, cyano, hydroxyl, $C_{1-6}$alkyl, $C_{1-6}$alkylsulphonyl, sulphonyl or $C_{1-5}$alkylCOOR$_7$.

In one embodiment, X is $C(CH_3)_2$, O or S.

In one embodiment,

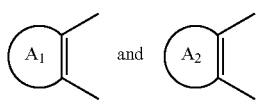

are each independently selected from at least one of the following:

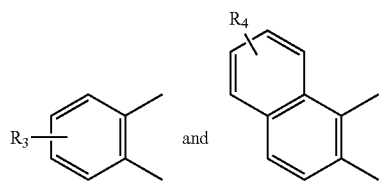

In one embodiment, $Z^-$ is selected from at least one of the following: halogen ions, $ClO_4^-$, $PF_6^-$, $CF_3SO_3^-$, $BF_4^-$, acetate and p-toluenesulfonate anions.

In one embodiment, a compound of general formula I is selected from Dye-1, Dye-2, Dye-3, Dye-4, Dye-5 or Dye-6, wherein such dyes have the following structures:

DYE-1

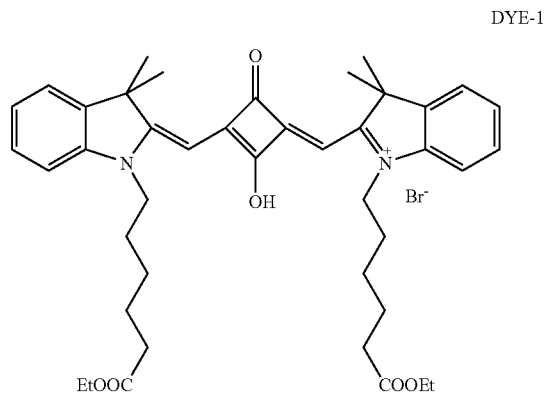

DYE-2

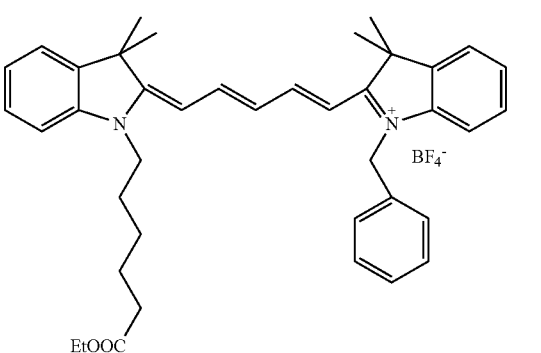

DYE-3

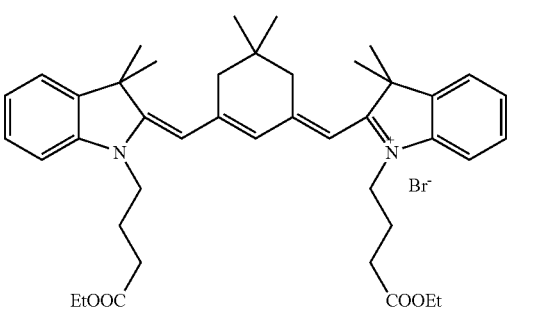

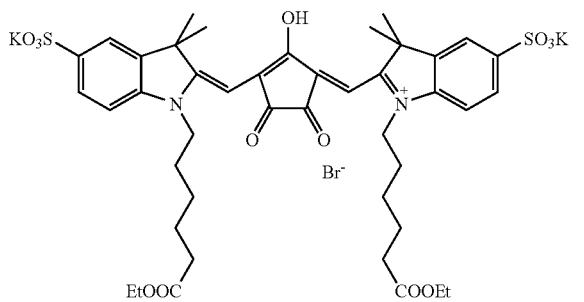
DYE-4

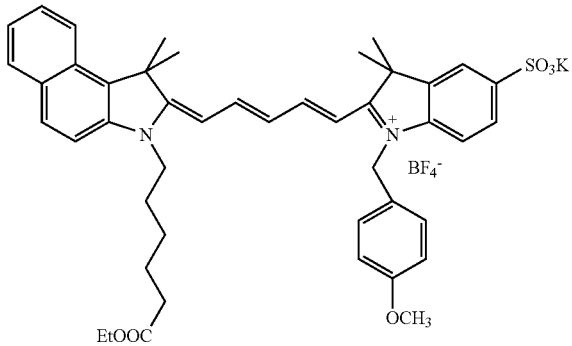
DYE-5

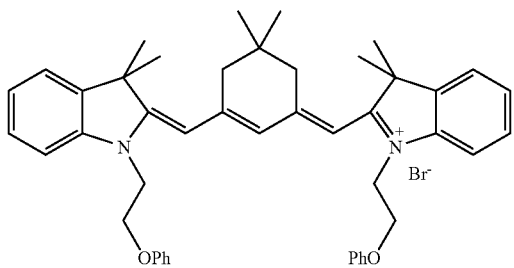
DYE-6

The compound having the general formula I is present in the reagent for blood analysis according to the present disclosure in a suitable concentration between 0.01 ppm and 1000 ppm. In one embodiment, the suitable range is 0.1 ppm to 100 ppm. In another embodiment, the suitable range is 1 ppm to 50 ppm.

The compound having the general formula I can be directly used for staining biological samples in the form of salts as described herein. Alternatively, in one embodiment, the compound having the general formula I can be used in the form of derivatives thereof, said derivatives including, but not limited to, conjugates.

Typically, conjugates are used in the fluorescence activated cell sorter (FACS). "Conjugates" as used herein refer to compounds formed by attaching the compound having the general formula I to other molecules via covalent bonds. Molecules that can be conjugated with the compound having the general formula I may be those that specifically bind to cells or cell components, including, but not limited to, antibodies, antigens, receptors, ligands, enzymes, substrates, coenzymes and the like. Generally, a test sample is incubated with a conjugate for a period of time so that the conjugate binds specifically to certain cells or cell components in the sample. The binding of the conjugate to the cells or cell components can also be referred to as staining. The above staining step can be repeated in sequence for several times, or a variety of conjugates can be used for concurrent multistaining. After the completion of staining, the sample is analyzed in a fluorescence activated cell sorter wherein an excitation light source excites the compound having the general formula I in the conjugate and a detection apparatus detects the emitted light generated by the excited compound.

Alternatively, in another embodiment, the conjugates can also be used in solid phase immunological assays, e.g. sandwich immunological assays. The techniques of solid phase immunological assays are well-known in the art and can be found in standard textbooks. Said conjugates can be used as various suitable components in solid phase immunological assays.

A specific description about the compound having the general formula I according to the present disclosure can be found in co-pending Chinese Invention Patent Application No. 200810217140.9 entitled "CYANINE COMPOUNDS AND THEIR USE IN STAINING BIOLOGICAL SAMPLES", which is incorporated herein by reference.

Surfactants

The surfactants as used in the present disclosure can be selected from cationic surfactants, nonionic surfactants or combinations thereof.

The cationic surfactants useful in the present disclosure may be quaternary ammonium salt-type cationic surfactants having the following general formula II:

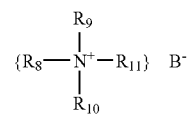

wherein $R_8$ is alkyl or alkenyl having 6 to 14 carbon atoms;

$R_9$ and $R_{10}$ are alkyl or alkenyl having 1 to 4 carbon atoms;

$R_{11}$ is alkyl or alkenyl having 1 to 4 carbon atoms, or benzyl;

B is a halogen atom.

In one embodiment, $R_8$ is selected from at least one of the following: straight-chain hexyl, octyl, decyl, dodecyl and myristyl group, particularly straight-chain decyl, dodecyl or myristyl group.

In one embodiment, $R_9$ and $R_{10}$ are selected from at least one of the following: methyl, ethyl, propyl and butenyl group and the like, particularly methyl, ethyl, or propyl group.

In one embodiment, B is a chlorine or bromine atom.

In one embodiment, the nonionic surfactants useful in the present disclosure are selected from at least one of the following: octylphenylpolyoxyethylene ether, polyoxyethylene(10)cetyl ether, polyoxyethylene(23)cetyl ether, polyoxyethylene(25)cetyl ether and polyoxyethylene(30)cetyl ether and the like, particularly polyoxyethylene(25)cetyl ether.

The surfactants are generally used in the reagent system according to the present disclosure in an amount of 50-5000 mg/L. In one embodiment, the surfactants are used in an amount of 100-2000 mg. The specific amount to be used can be suitably adjusted depending on the kind of the surfactant used. Any kind of surfactant can be used as long as hemolytic activity thereof is capable of lysing the membrane of erythrocytes as well as generating pores in the membrane of leukocytes so that fluorescent dye can enter the leukocytes. In one embodiment, it is used in an amount far lower than that which renders the nuclei of leukocytes naked. The hemolytic effect of surfactants is correlated with the length of side chains. The longer the side chains, the lower the concentration needed.

Other Components

The reagent for blood analysis according to the present disclosure may also comprise an aromatic organic acid or salts thereof for speeding up lysis of erythrocytes. In one embodiment, salicylic acid and salts thereof are used. In another embodiment, benzoic acid and salts thereof are used. The concentration used is in a range of 1-100 mmol/L.

The reagent for blood analysis according to the present disclosure may also comprise a buffering agent for adjusting the pH. Buffering agents commonly used are citric acid, formic acid, acetic acid, glycine, phthalic acid, tartaric acid, malic acid, and maleic acid etc. They are generally used in a concentration of 0.01-0.1 mol/L, for example 0.01-0.05 mol/L. By using the buffering agent, the pH value of the reagent for blood analysis according to the present disclosure can be generally maintained in a range of 2-6, such as 2.5-4.5.

The reagent for blood analysis according to the present disclosure may also comprise an antioxidant, commonly 2,6-di-tert-butyl-4-methylphenol, 4-methoxyphenol, sodium erythorbate or vitamins, etc. The antioxidant is generally used in a concentration of 0.1-5 g/L.

The reagent for blood analysis according to the present disclosure may also comprise an osmotic regulating agent for regulating osmotic pressure. The osmotic pressure of the reagent for blood analysis according to the present disclosure may be maintained in a range of 20-150 mOsm/kg, since an osmotic pressure in this range will result in erythrocytes being easily lyzed so that the interference of erythrocytes with detection may be prevented. Commonly used alkali metal salts, glucose and mannitol can all maintain the osmotic pressure of the reagent for blood analysis according to the present disclosure within a reasonable range.

In addition, where the compound having the general formula I according to the present disclosure is unstable in aqueous solutions, it can be dissolved and stored in such solvents as methanol, ethanol, dimethylsulfoxide and glycol, and afterwards mixed with the aqueous solutions of other components prior to use.

Kit for Blood Analysis According to the Present Disclosure

In another aspect of the present disclosure there is provided a use of the reagent for blood analysis according to the present disclosure in the manufacture of a kit useful for differentiating and counting blood cells. In some embodiments, said kit is effective for identifying and counting erythroblasts and/or basophils in a blood sample to be detected, and meanwhile counting leukocytes therein.

In still another aspect of the present disclosure there is provided a kit comprising the reagent for blood analysis according to the present disclosure. Said kit is useful for differentiating and counting blood cells. In some embodiments, said kit is effective for identifying and counting erythroblasts and/or basophils in a blood sample to be detected, and meanwhile counting leukocytes therein.

In an embodiment of the kit, the compound having the general formula I is stored as a stock solution in a separate container. In some embodiments, methanol, ethanol, dimethylsulfoxide, glycol or the like are used as solvents for the stock solution. Prior to use, the stock solution can be mixed with the aqueous solutions of other components.

In another embodiment of the kit, the compound having the general formula I is formulated with the above-said surfactants and/or other components as a single solution.

Said kit may also comprise other reagents for the differentiation and counting of blood cells, particularly erythroblasts, basophils and leukocytes, as well as instructions regarding the method of performing said differentiation and counting. Said kit may further comprise a control sample or a series of control samples that can be detected and compared to a test sample. The various components of the kit can be respectively contained in individual containers, and the containers, together with the instructions, can be housed in a single package.

The Method of Using the Reagent for Blood Analysis to Perform Differentiating and Counting Blood Cells In yet another aspect of the present disclosure there is provided a method for differentiating and counting blood cells, said method comprising the following steps: (a) mixing a blood sample with the reagent for blood analysis according to the present disclosure to form a cell suspension; (b) detecting scattered light signals and fluorescence signals from cells in the cell suspension; and (c) differentiating and counting the cells in the blood sample in terms of the scattered light signals and fluorescence signals.

The analysis process using the reagent includes: mixing the reagent according to the present disclosure and a test sample for a period of time, detecting information regarding the fluoresce intensity and size of the cells, and differentiating erythroblasts, basophils and other subpopulation of leukocytes. Moreover, as erythroblasts at different developmental stages have different sizes of nuclei, the reagent according to the present disclosure can further differentiate erythroblasts into subpopulations at different developmental stages.

When using the reagent according to the present disclosure to treat a test sample, the compound having the general formula I and a hemolytic agent containing surfactants can be added to and mixed with the test sample at the same time, or they can be added to and mixed with the test sample in sequence.

When analyzing blood cells by the reagent for blood analysis according to the present disclosure on a flow cytometer or a fully automatic blood cell analyzer, in one embodiment, a blood sample and the reagent for blood analysis according to the present disclosure are first mixed in a certain ratio, for example 1:10-1:100, to homogeneity to prepare a cell suspension, and then the cell suspension is incubated at a reaction temperature of 42° C. for 4-30 seconds. Afterwards the cell suspension is injected into an optical system as shown in FIG. 1 for detection.

In the above-said optical system, individual cells are sequentially passed into the flow chamber and irradiated by the laser whose wavelength is about 630 nm emitted from the semiconductor laser. The fluorescent dye used in the reagent for blood analysis according to the present disclosure is capable of being excited at about 640 nm and its wavelength can remain stable at 42° C., thus matching the working wavelength of the semiconductor laser used.

Subsequently, the scattered light signals emitted from the excited cells are collected by the photodiode. The collection angle can be a low angle) (0°-5° or a high angle) (6°-20°. The fluorescence signals emitted from the cells are collected by the laterally disposed photomultiplier tube.

Then the scattered light signals and the fluorescence signals are input into a data processing unit for analysis. Finally, the various kinds of cells in the blood are differentiated and counted based upon the scattered light signals and fluorescence signals emitted from the cells.

EXAMPLES

The present disclosure is further illustrated by the following particular examples to which or by which the present disclosure is not limited.

Unless otherwise stated, the detection apparatus used in the following examples for detecting blood cells is the BC series flow cytometer manufactured by Shenzhen Mindray Bio-Medical Electronics Co. Ltd (Shenzhen, People's Republic of China), with the detection wavelength being 640 nm. The schematic diagram of the cell analyzer is shown in FIG. 1.

Example 1

One example of the reagent for blood analysis according to the present disclosure has the following components:

| | |
|---|---|
| The compound having the general formula I (fluorescent dye) | 10 mg |
| Citric acid | 1.21 g |
| Dodecyltrimethylammonium chloride | 500 mg |
| Sodium salicylate | 1.6 g |
| 4-methoxyphenol | 0.2 g |
| $H_2O$ | to a volume of 1 L |
| (Adjust the pH value of the reagent to about 3.5 with HCl) | |

The compound having the general formula I used in this example as the fluorescent dye has the following structure:

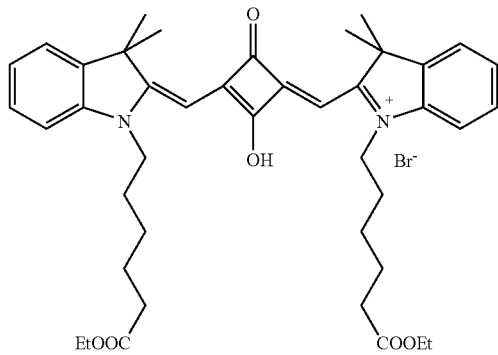

Figure 2:
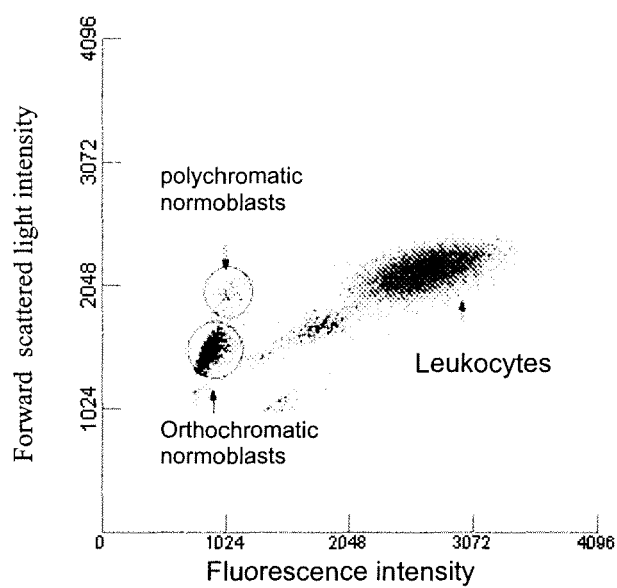
FIG. 2 is a scattergram formed by plotting forward scattered light intensity against fluorescence intensity of peripheral blood measured using the reagent for blood analysis according to one embodiment of the present disclosure (Example 1).

A blood sample having erythroblasts in high value was taken, which has 22 erythroblasts/100 leukocytes as determined by the Wright-Giemsa staining method recommended by the International Committee for Standardization of Hematology (ICSH). 20 μL of the blood sample was mixed with 1 mL of the above reagent to homogeneity to form a cell suspension and then the suspension was incubated at 42° C. for 4.8 seconds. Afterwards the cell suspension was passed through the flow cytometer, forward) (0° scattered light signals and fluorescence signals of the cells were detected to generate a scattergram as shown in FIG. 2. In the scattergram, there is an obvious demarcation between erythroblasts and leukocytes, with erythroblasts accounted for 22.24%.

The reagent of the present example can further differentiate erythroblasts into polychromatic normoblasts and orthochromatic normoblasts. The ratio of the polychromatic normoblasts in the blood sample was 2% (2 polychromatic normoblasts/100 leukocytes) and that of the orthochromatic normoblasts was 20% (20 orthochromatic normoblasts/100 leukocytes) as determined by the Wright-Giemsa staining method recommended by the ICSH. Similarly, from the scattergram obtained by the reagent and the method of the present example, the polychromatic normoblasts accounted for 2.15% and the orthochromatic normoblasts 20.09%.

Example 2

Figure 3:
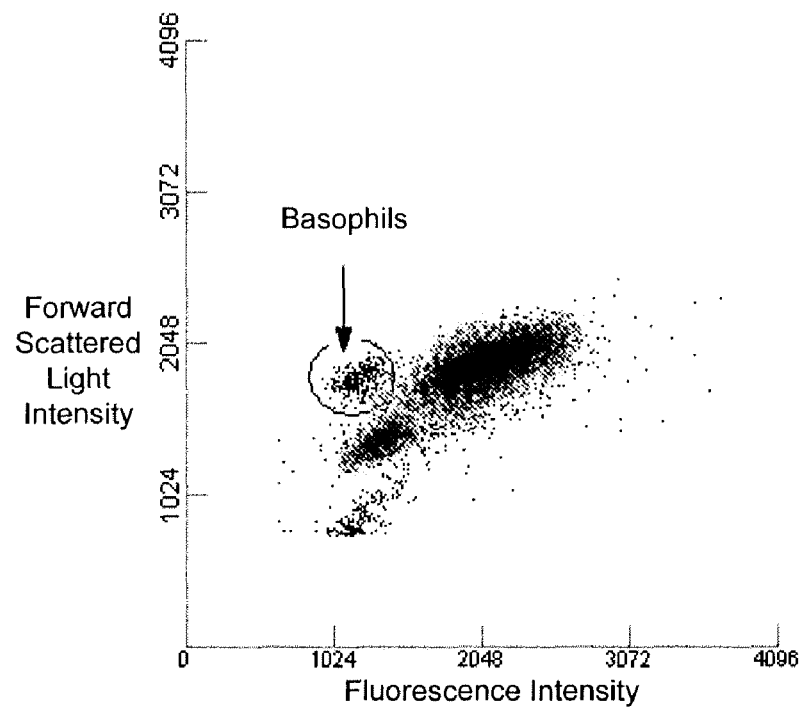
FIG. 3 is a scattergram formed by plotting forward scattered light intensity against fluorescence intensity of peripheral blood measured using the reagent for blood analysis according to one embodiment of the present disclosure (Example 2).

A blood sample having basophils in a relatively high value was taken, which has 5% basophil as determined by the Wright-Giemsa staining method recommended by the ICSH. The sample was analysis using the reagent and the method as described Example 1, and the scattergram as shown in FIG. 3 was generated. In the scattergram, there is an obvious demarcation between basophils and other leukocytes, with basophils accounted for 4.61%.

Example 3

One example of the reagent for blood analysis according to the present disclosure has the following components:

| | |
|---|---|
| The compound having the general formula I (fluorescent dye) | 10 mg |
| Citric acid | 1.21 g |
| Polyoxyethylene(25)cetyl ether | 500 mg |
| Sodium salicylate | 1.6 g |
| 2,6-di-tert-butyl-4-methylphenol | 0.2 g |
| $H_2O$ | to a volume of 1 L |
| (Adjust the pH value of the reagent to about 3.5 with HCl) | |

The compound having the general formula I used in this example as the fluorescent dye has the following structure:

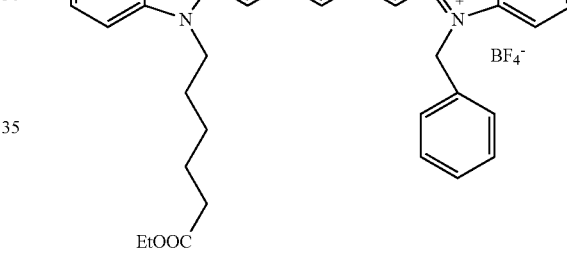

Figure 4:
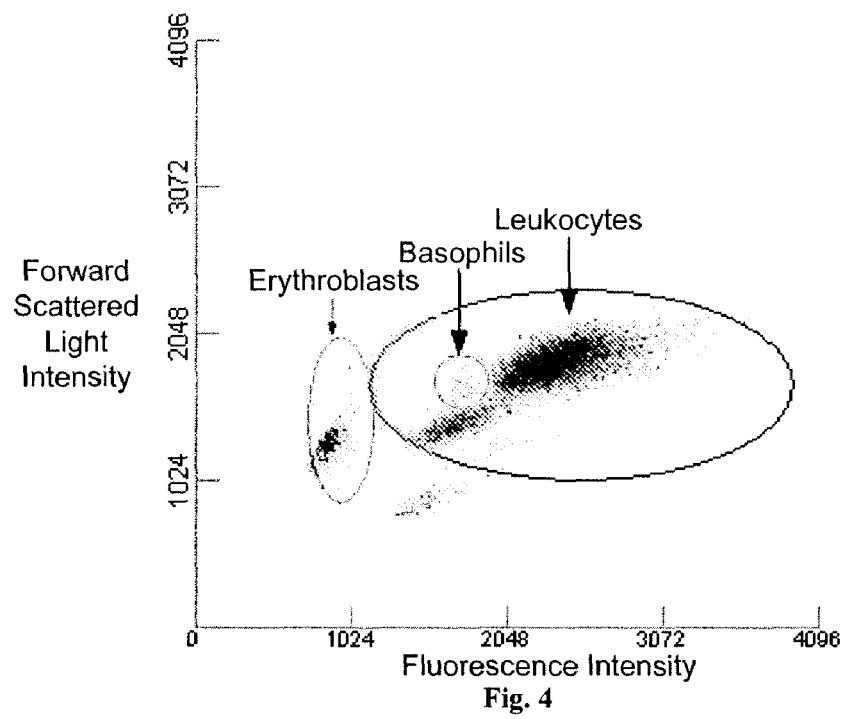
FIG. 4 is a scattergram formed by plotting forward scattered light intensity against fluorescence intensity of peripheral blood measured using the reagent for blood analysis according to one embodiment of the present disclosure (Example 3).

20 μL of the blood sample was mixed with 1 mL of the above reagent to homogeneity to form a cell suspension and then the suspension was incubated at 42° C. for 4 seconds. Afterwards the cell suspension was passed through the flow cytometer and the forward) (0° scattered light signals and fluorescence signals of the cells were detected to generate a scattergram as shown in FIG. 4, from which erythroblasts accounted for 5.6% and basophils 1.2%. The same sample was determined by the Wright-Giemsa staining method recommended by the ICSH as having 5% erythroblasts (5 erythroblasts/100 leukocytes) and 1% basophils.

Example 4

One example of the reagent for blood analysis according to the present disclosure has the following components:
(Part 1 of the Reagent)

| | |
|---|---|
| Citric acid | 1.21 g |
| Dodecyltrimethylammonium chloride | 400 mg |
| Sodium benzoate | 2.0 g |
| 4-methoxyphenol | 0.2 g |
| $H_2O$ | to a volume of 1 L |
| (Adjust the pH value of the reagent to about 3.5 with HCl) | |

-continued

| (Part 2 of the Reagent) | |
|---|---|
| The compound having the general formula I (fluorescent dye) | 10 mg |
| Methanol | 5 ml |
| Glycol | 95 ml |

The compound having the general formula I used in this example as the fluorescent dye has the following structure:

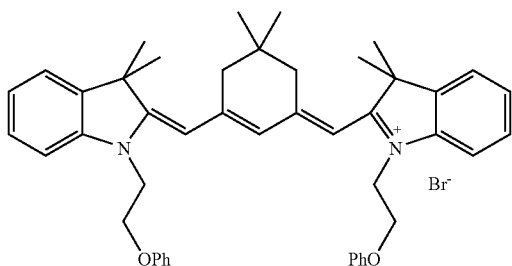

Figure 5:
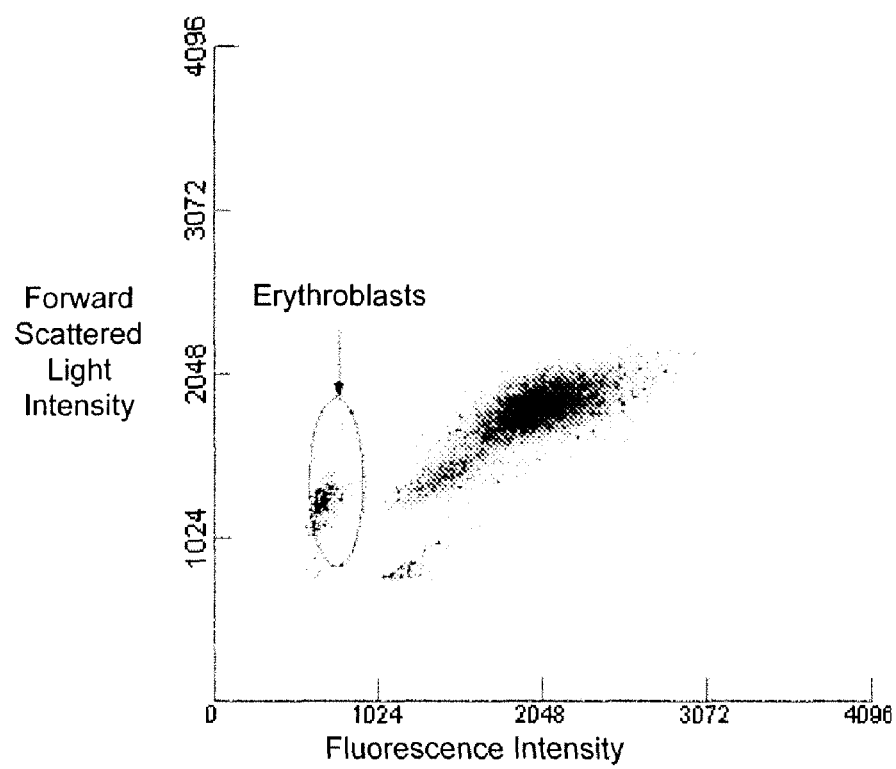
FIG. 5 is a scattergram formed by plotting forward scattered light intensity against fluorescence intensity of peripheral blood measured using the reagent for blood analysis according to one embodiment of the present disclosure (Example 4).

A blood sample having erythroblasts in high value of was taken, and 20 μL of the blood sample was mixed with 1 mL of the above Part 1 of the reagent to homogeneity followed by addition of the above Part 2 of the reagent to form a cell suspension. Then the cell suspension was incubated at 42° C. for 3 seconds. Afterwards the cell suspension was passed through the flow cytometer and the forward) (0° scattered light signals and fluorescence signals of the cells were detected to generate a scattergram as shown in FIG. 5, in which erythroblasts accounted for 4.5% and basophils 0.1%. The same sample was determined by the Wright-Giemsa staining method recommended by the ICSH as having 4% erythroblasts (4 erythroblasts/100 leukocytes) and 0% basophils.

Example 5

One example of the reagent for blood analysis according to the present disclosure has the following components:

| The compound having the general formula I (fluorescent dye) | 10 mg |
|---|---|
| Citric acid | 1.21 g |
| Tetradecyltrimethylammonium chloride | 100 mg |
| Sodium salicylate | 1.6 g |
| 4-methoxyphenol | 0.2 g |
| H$_2$O | to a volume of 1 L |
| (Adjust the pH value of the reagent to about 3.5 with HCl) | |

The compound having the general formula I used in this example as the fluorescent dye has the following structure:

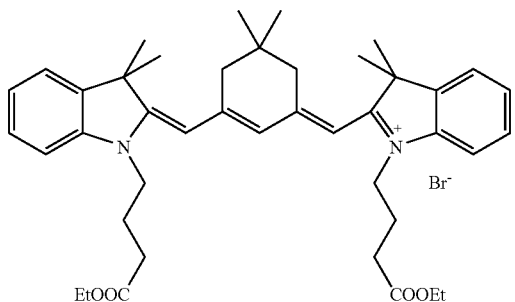

Figure 6:
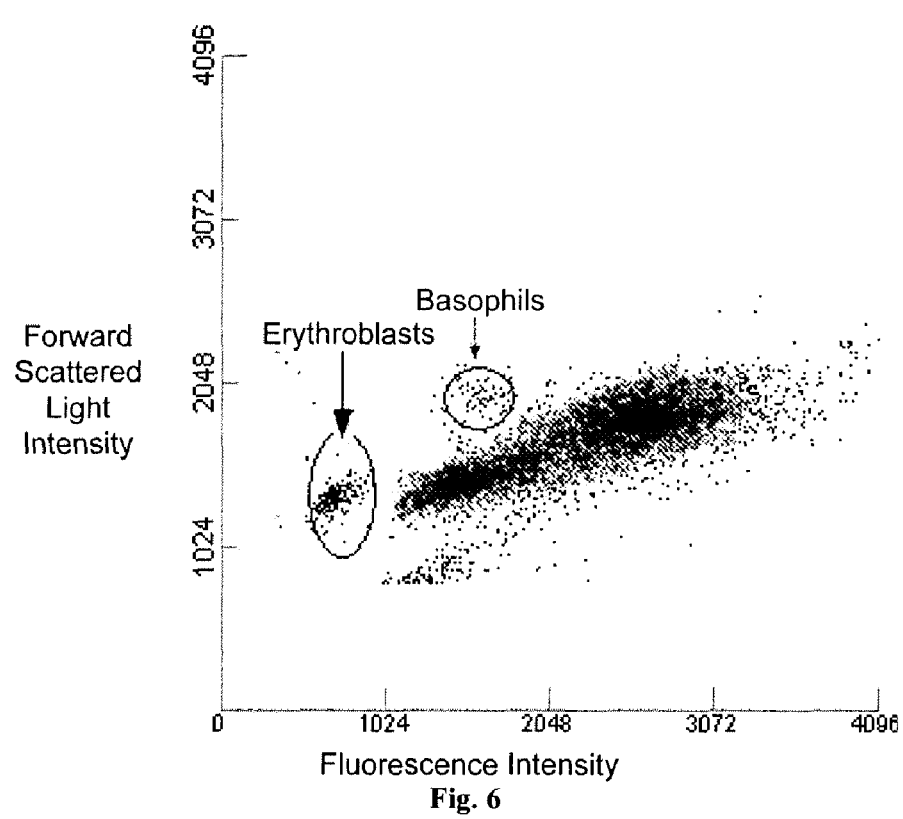
FIG. 6 is a scattergram formed by plotting forward scattered light intensity against fluorescence intensity of peripheral blood measured using the reagent for blood analysis according to one embodiment of the present disclosure (Example 5).

A blood sample having erythroblasts was taken, which had 4% erythroblasts (4 erythroblasts/100 leukocytes) and 1% basophils as determined by the Wright-Giemsa staining method recommended by the ICSH. 20 μL of the blood sample was mixed with 1 mL of the above reagent to homogeneity to form a cell suspension and then the suspension was incubated at 42° C. for 4.8 seconds. Afterwards the cell suspension was passed through the flow cytometer and the forward) (0° scattered light signals and fluorescence signals of the cells were detected to generate a scattergram as shown in FIG. 6, in which erythroblasts accounted for 4.5% and basophils 0.7%.

Example 6

One example of the reagent for blood analysis according to the present disclosure has the following components:

| The compound having the general formula I (fluorescent dye) | 10 mg |
|---|---|
| Citric acid | 2.1 g |
| Dodecyltrimethylammonium chloride | 300 mg |
| Sodium salicylate | 2.0 g |
| Sodium metabisulfite | 0.2 g |
| H$_2$O | to a volume of 1 L |
| (Adjust the pH value of the reagent to about 3.5 with HCl) | |

The compound having the general formula I used in this example as the fluorescent dye has the following structure:

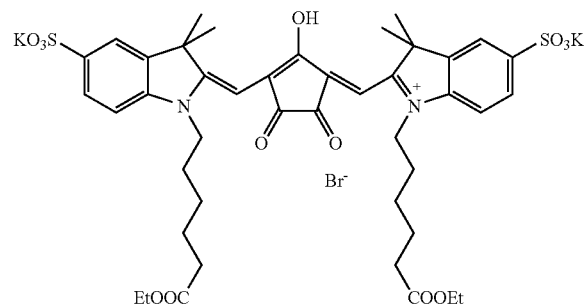

Figure 7:
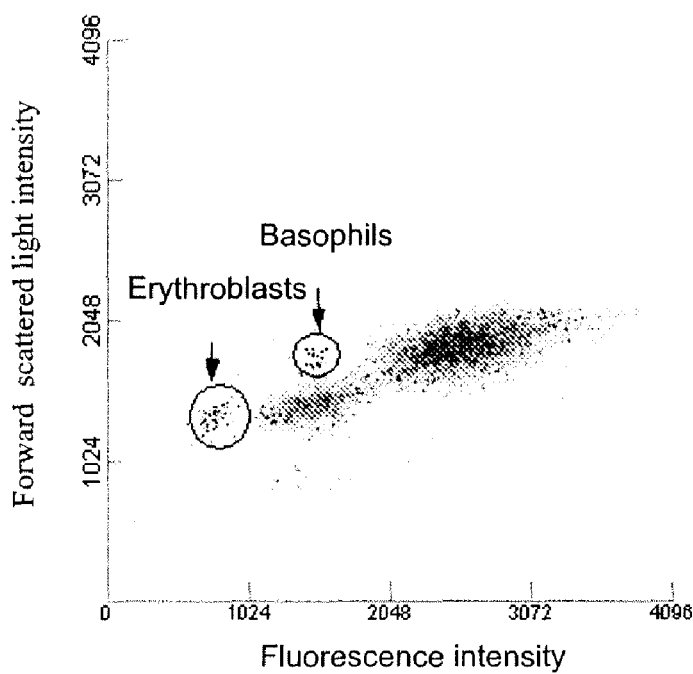
FIG. 7 is a scattergram formed by plotting forward scattered light intensity against fluorescence intensity of peripheral blood measured using the reagent for blood analysis according to one embodiment of the present disclosure (Example 6).

A blood sample having erythroblasts was taken, which had 4% erythroblasts (4 erythroblasts/100 leukocytes) and 1% basophils as determined by the Wright-Giemsa staining method recommended by the ICSH. 20 μL of the blood sample was mixed with 1 mL of the above reagent to homogeneity to form a cell suspension and then the suspension was incubated at 42° C. for 4.8 seconds. Afterwards the cell suspension was passed through the flow cytometer and the forward) (0° scattered light signals and fluorescence signals of the cells were detected to generate a scattergram as shown in FIG. 7, in which erythroblasts accounted for 3.8% and basophils 0.8%.

Example 7

One example of the reagent for blood analysis according to the present disclosure has the following components:

| | |
|---|---|
| The compound having the general formula I (fluorescent dye) | 10 mg |
| Citric acid | 2.52 g |
| Sodium citrate | 0.88 g |
| Dodecyltrimethylammonium chloride | 300 mg |
| Sodium salicylate | 1.6 g |
| 4-methoxyphenol | 0.2 g |
| H₂O | to a volume of 1 L |
| (Adjust the pH value of the reagent to about 3.5 with HCl) | |

The compound having the general formula I used in this example as the fluorescent dye has the following structure:

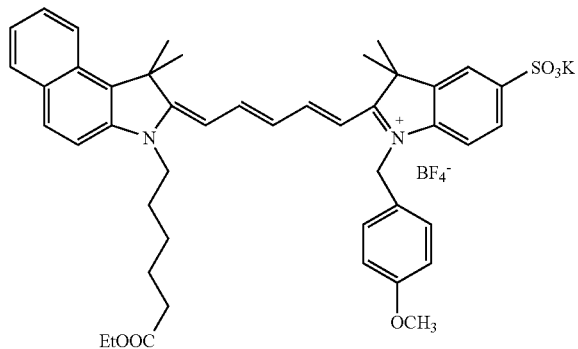

Figure 8:
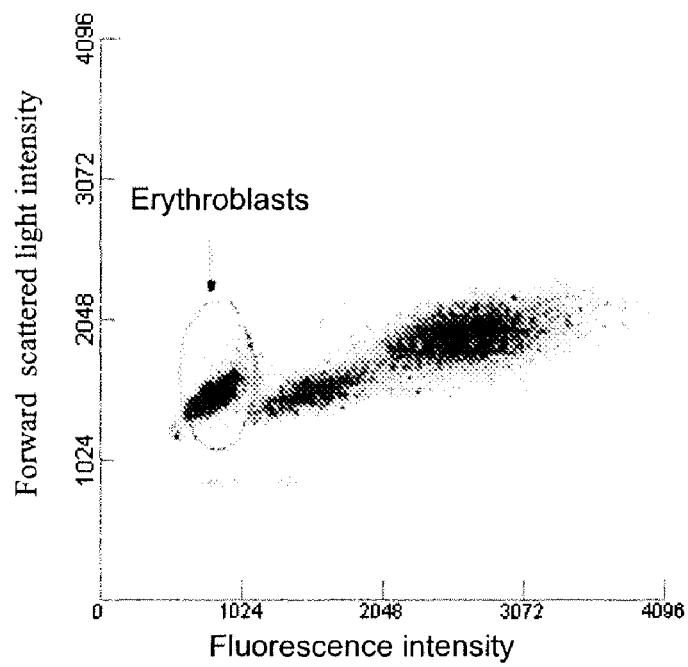
FIG. 8 is a scattergram formed by plotting forward scattered light intensity against fluorescence intensity of peripheral blood measured using the reagent for blood analysis according to one embodiment of the present disclosure (Example 7).

A blood sample having a high level of erythroblasts was taken, which had 39% erythroblasts (39 erythroblasts/100 leukocytes) as determined by the Wright-Giemsa staining method recommended by the ICSH. 20 μL of the blood sample was mixed with 1 mL of the above reagent to homogeneity to form a cell suspension and then the suspension was incubated at 42° C. for 4.8 seconds. Afterwards the cell suspension was passed through the flow cytometer and the forward) (0° scattered light signals and fluorescence signals of the cells were detected to generate a scattergram as shown in FIG. 8, in which erythroblasts accounted for 38.6%.

Example 8

Figure 9:
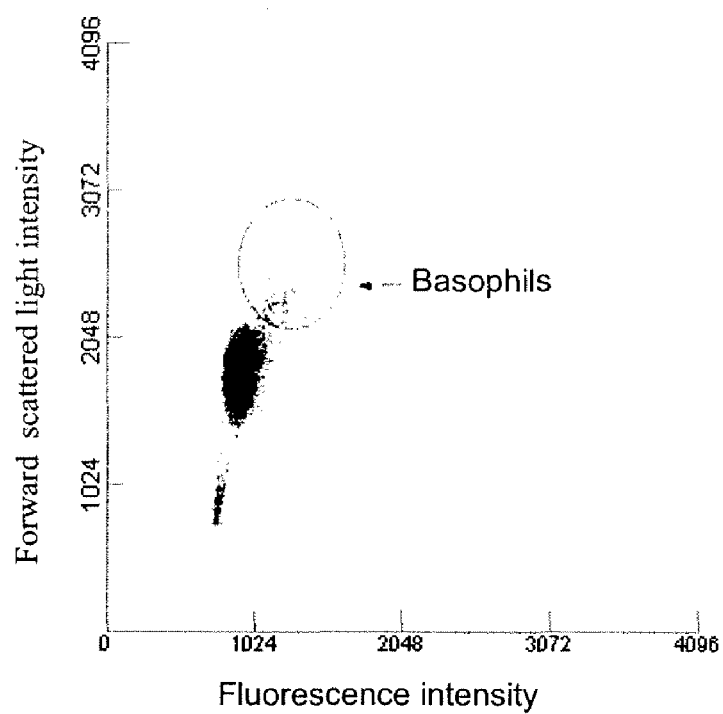
FIG. 9 is a scattergram formed by plotting forward scattered light intensity against fluorescence intensity of peripheral blood measured using the reagent for detecting basophils disclosed in U.S. Pat. No. 5,518,928 (Example 8).
Figure 10:
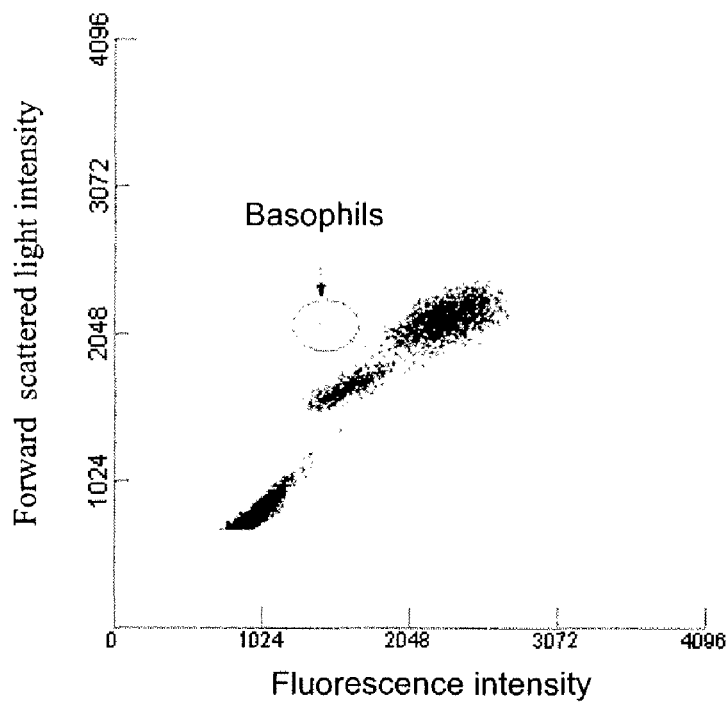
FIG. 10 is a scattergram formed by plotting forward scattered light intensity against fluorescence intensity of peripheral blood measured using the reagent for blood analysis according to one embodiment of the present disclosure (Example 8).

A clinical blood sample was taken and treated with the reagent for detecting basophils disclosed in U.S. Pat. No. 5,518,928 to form a cell suspension which was then passed through the flow cytometer. The impedance of or the low-angle scattered light from the cells was detected to obtain signals representing cell size, and the side or high-angle scattered light from the cells was detected to obtain signals representing intracellular structure. By combining these two kinds of signals, the counting of basophils was achieved, with the basophil accounted 2.5%, as shown in FIG. 9. In contrast, the blood sample had 0.5% basophils as determined by the Wright-Giemsa staining method recommended by the ICSH. Evidently, the detection result obtained by the light scattering method is markedly higher than that obtained by the Wright-Giemsa staining method. Microscopic examination of the sample revealed that it had 3% immature granulocytes and some of them were large in size, had increased granulated substances in the cytoplasm which was stained dark blue. This indicates that the occurrence of immature granulocytes in the blood sample due to some disorders may cause a false increase in the number of basophils detected by the light scattering method. Since immature granulocytes have a higher content of nucleic acids than basophils, they can be distinguished from each other based upon the difference of their fluorescence intensity caused by binding with the fluorescent dye. Therefore, by using the reagent and the method of Example 1 according to the present disclosure, the blood sample was measured and basophils accounted for 0.6%, as shown in FIG. 10, which result was similar to that obtained by the Wright-Giemsa staining method recommended by the ICSH.

Example 9

Figure 11:
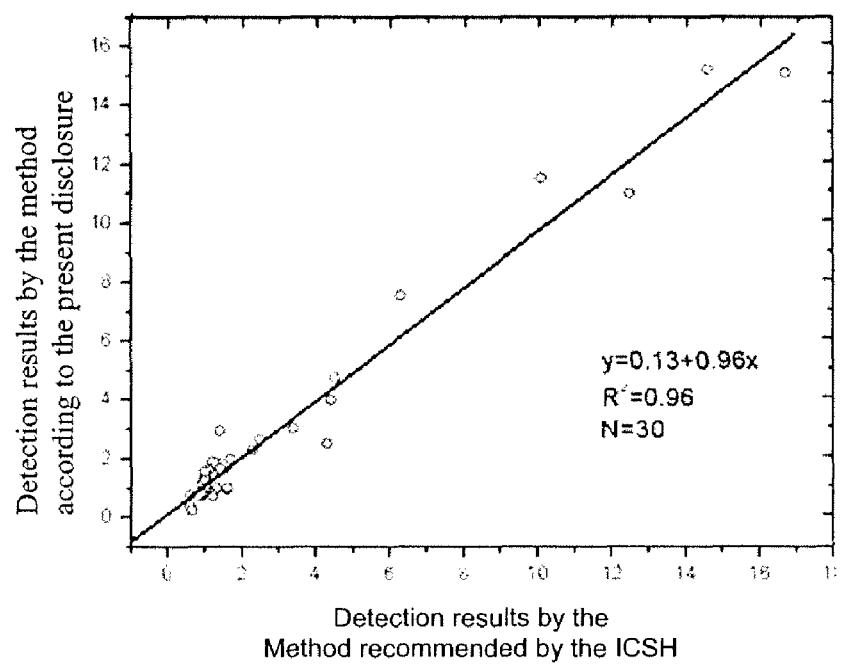
FIG. 11 is a graph which shows the correlation between the percentage results of basophil obtained by the analysis method in an embodiment of the present disclosure and those obtained by the method recommended by International Committee for Standard of Hematology (ICSH) (Example 9).
Figure 12:
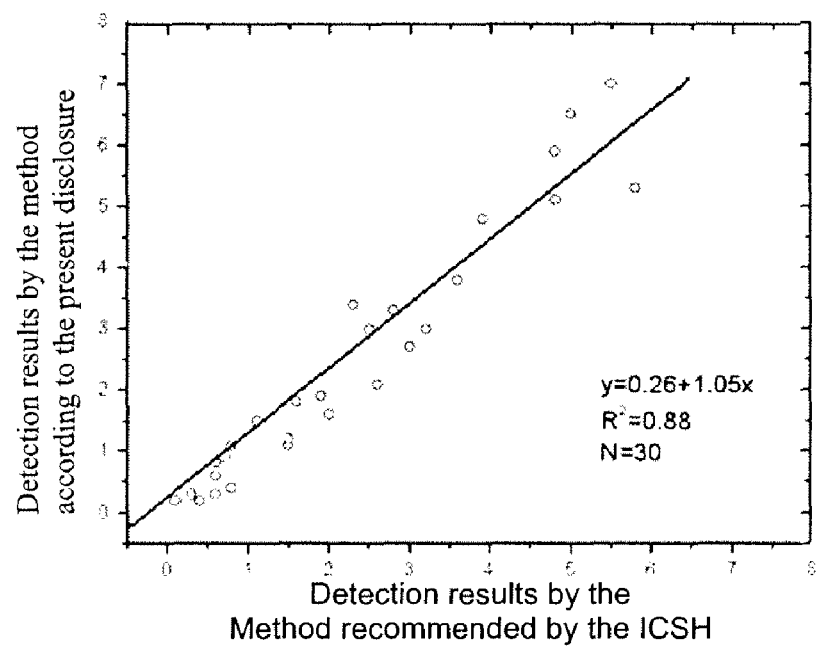
FIG. 12 is a graph which shows the correlation between the percentage results of erythroblast obtained by the analysis method in an embodiment of the present disclosure and those obtained by the standard method recommended by the International Committee for Standardization of Hematology (ICSH) (Example 9).

Thirty (30) clinical blood samples were taken, and the basophils in these samples were respectively detected by the method as described in Example 1 and the Wright-Giemsa staining method recommended by the ICSH. The correlation of the detection results is shown in FIG. 11. Thirty (30) erythroblast samples were taken, and the erythroblasts were respectively detected by the method as described in Example 1 and the Wright-Giemsa staining method recommended by the ICSH. The correlation of the detection results is shown in FIG. 12.

Although the present disclosure has been illustrated by way of the above embodiments and particular examples thereof, it will be appreciated by those skilled in the art that various changes, alterations and modifications may be made to the present disclosure without departing from the spirit and scope of the present disclosure as defined by the appended claims.

The invention claimed is:
1. A reagent for blood analysis, said reagent comprising:
(1) a compound having the general formula I:

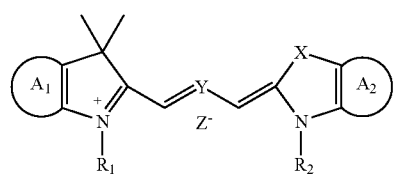

wherein
$R_1$ and $R_2$ are each independently selected from at least one of the following: $C_{1-18}$malkylCOOR$_6$, $C_{1-18}$alkylOR$_6$ and benzyl, wherein said benzyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl, provided that $R_1$ and $R_2$ are not all simultaneously benzyl;
$R_6$ in each occurrence is independently $C_{1-18}$alkyl or phenyl, wherein said phenyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;
Y is —CH—CH=C—,

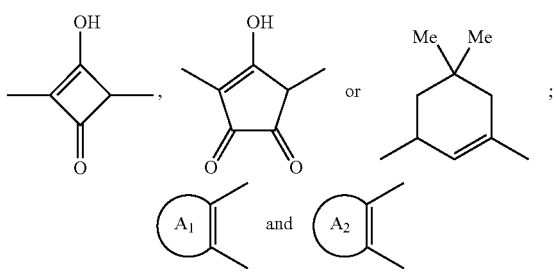

are each independently

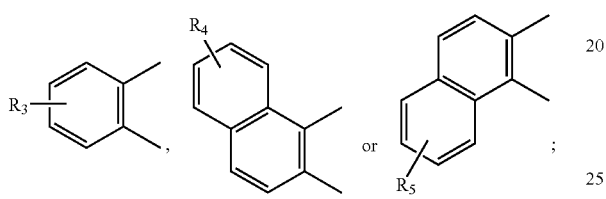

$R_3$, $R_4$ and $R_5$ are each independently selected from at least one of the following: H, halogen, cyano, hydroxyl, $C_{1-18}$alkyl, $C_{1-18}$alkylsulphonyl, sulphonyl and $C_{1-5}$alkylCOOR$_7$;
$R_7$ is H or $C_{1-6}$alkyl; and
$Z^-$ is an anion;
wherein the compound of formula I is present in a concentration of from about 0.01 ppm to about 1000 ppm and configured to permit detection of erythroblasts and basophils; and
(2) at least one surfactant selected from cationic surfactants and nonionic surfactants, wherein
the cationic surfactant is selected from quaternary ammonium salt-type cationic surfactants having the following general formula II:

$$\{R_8-\overset{R_9}{\underset{R_{10}}{N^+}}-R_{11}\}\ B^-\qquad II$$

wherein
$R_8$ is alkyl or alkenyl having 6 to 14 carbon atoms;
$R_9$ and $R_{10}$ are alkyl or alkenyl having 1 to 4 carbon atoms;
$R_{11}$ is alkyl or alkenyl having 1 to 4 carbon atoms, or benzyl; and
B is a halogen atom; and
the nonionic suractant is selected from at least one of the following: octylphenylpolyoxyethylene ether, polyoxyethylene(10)cetyl ether, polyoxyethylene(23)cetyl ether, polyoxyethylene(25)cetyl ether and polyoxyethylene(30)cetyl ether;
wherein the at least one surfactant is present in a concentration of from about 50 mg/L to about 5000 mg/L and is configured to lyse erythrocytes.

2. The reagent for blood analysis according to claim 1, wherein $R_1$ and $R_2$ are each independently selected from at least one of the following: $C_{1-6}$alkylCOOR$_6$, $C_{1-6}$alkylOR$_6$ and benzyl, provided that $R_1$ and $R_2$ are not all simultaneously benzyl.

3. The reagent for blood analysis according to claim 1, wherein $R_6$ in each occurrence is independently $C_{1-6}$alkyl or phenyl.

4. The reagent for blood analysis according to claim 1, wherein $R_3$, $R_4$ and $R_5$ are each independently selected from at least one of the following: H, halogen, cyano, hydroxyl, $C_{1-6}$alkyl, $C_{1-6}$alkylsulphonyl, sulphonyl or $C_{1-5}$alkyl-COOR$_7$.

5. The reagent for blood analysis according to claim 1, wherein X is $C(CH_3)_2$, O or S.

6. The reagent for blood analysis according to claim 1, wherein

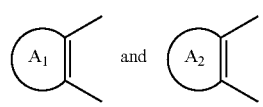

are each independently selected from at least one of the following:

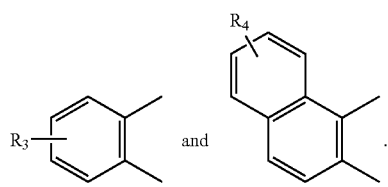

7. The reagent for blood analysis according to claim 1, wherein $Z^-$ is selected from at least one of the following: halogen ions, $ClO_4^-$, $PF_6^-$, $CF_3SO_3^-$, $BF_4^-$, acetate or p-toluenesulfonate anions.

8. The reagent for blood analysis according to claim 1, wherein said compound having general formula I is:

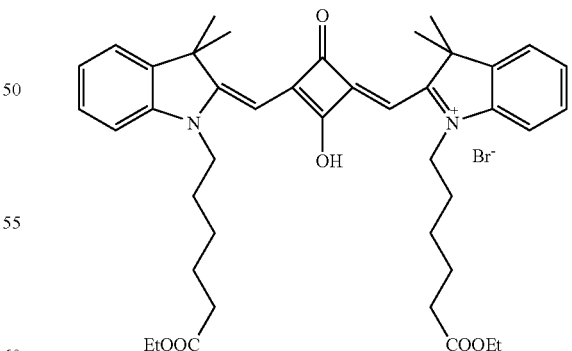

-continued

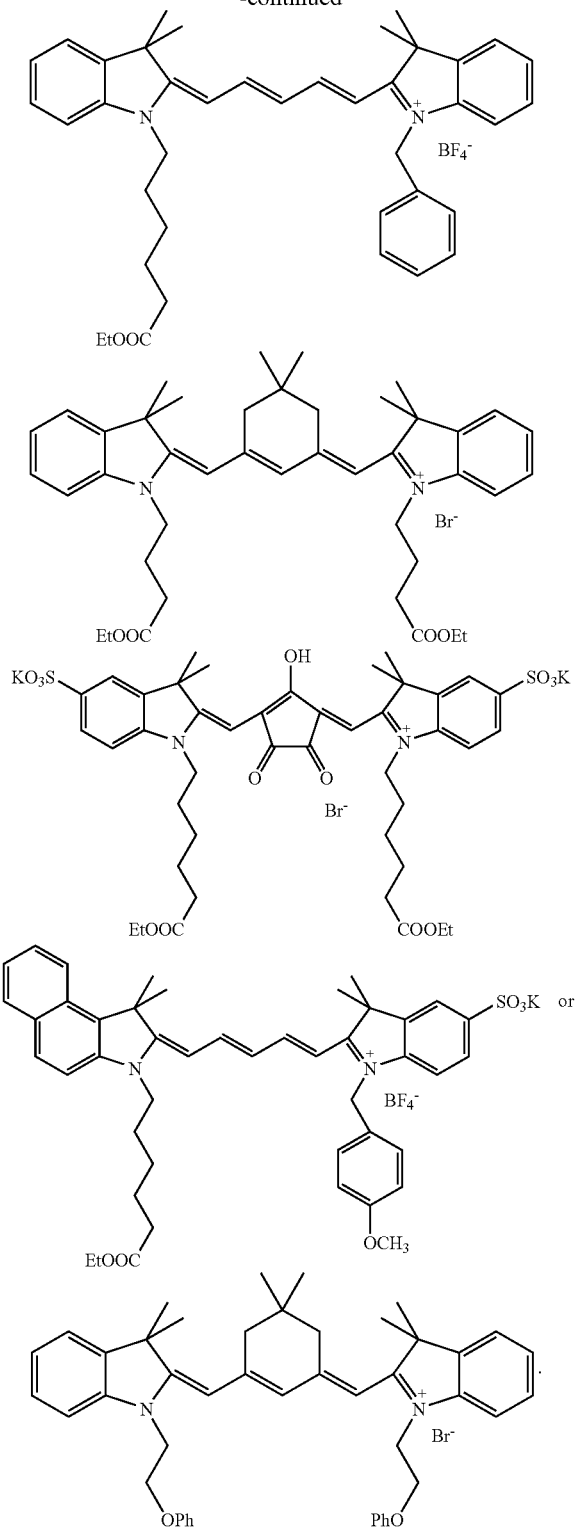

9. The reagent for blood analysis according to claim 1, wherein $R_8$ is selected from at least one of the following: straight-chain hexyl, octyl, decyl, dodecyl and myristyl group.

10. The reagent for blood analysis according to claim 1, wherein $R_9$ and $R_{10}$ are selected from at least one of the following: methyl, ethyl, propyl and butenyl group.

11. The reagent for blood analysis according to claim 1, wherein B is a chlorine or bromine atom.

12. The reagent for blood analysis according to claim 1, said reagent also comprises an aromatic organic acid or salts thereof.

13. The reagent for blood analysis according to claim 12, wherein said aromatic organic acid or salts thereof comprises salicylic acid and salts thereof and/or benzoic acid and salts thereof.

14. The reagent for blood analysis according to claim 1, said reagent also comprises a pH buffering agent selected from at least one of the following: citric acid, formic acid, acetic acid, glycine, phthalic acid, tartaric acid, malic acid, and maleic acid.

15. The reagent for blood analysis according to claim 14, wherein said buffering agent has a pH of between 2-6.

16. The reagent for blood analysis according to claim 15, wherein said buffering agent has a pH of between 2.5-4.5.

17. The reagent for blood analysis according to claim 1, said reagent also comprises an antioxidant selected from at least one of the following: 2,6-di-tert-butyl-4-methylphenol, 4-methoxyphenol, sodium erythorbate and vitamins.

18. The reagent for blood analysis according to claim 1, said reagent also comprises an osmotic regulating agent selected from at least one of the following:
alkali metal salts, glucose and mannitol.

19. The reagent for blood analysis according to claim 18, wherein the osmotic pressure of said reagent is maintained in a range of between 20-150 mOsm/kg.

20. A kit comprising the reagent for blood analysis according to claim 1, wherein said compound having the general formula I and said surfactant(s) are individually stored in separate containers.

21. A kit comprising the reagent for blood analysis according to claim 1, wherein said compound having the general formula I and said surfactant(s) are formulated as a single solution.

22. A reagent for blood analysis, said reagent comprising:
(1) a conjugate of the compound having the general formula I of claim 1; and
(2) at least one surfactant selected from cationic surfactants and nonionic surfactants.

23. A reagent for blood analysis, said reagent comprising:
(1) a compound having the general formula I:

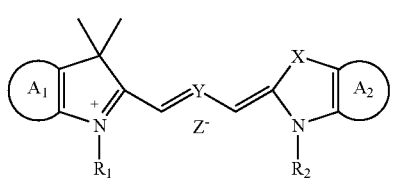

wherein
$R_1$ and $R_2$ are each independently selected from at least one of the following: $C_{1-18}$alkylCOOR$_6$, $C_{1-18}$alkylOR$_6$ and benzyl, wherein said benzyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl, provided that $R_1$ and $R_2$ are not all simultaneously benzyl;
$R_6$ in each occurrence is independently $C_{1-18}$alkyl or phenyl, wherein said phenyl is optionally substituted with a substituent selected from at least one of the following:

halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;

Y is —CH—CH=CH—,

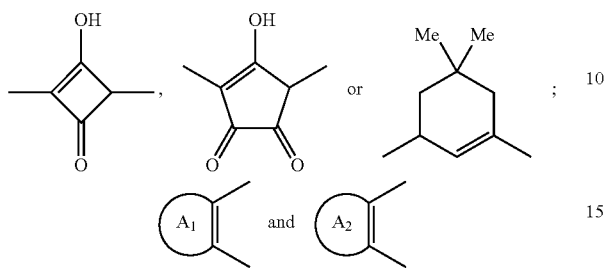

are each independently

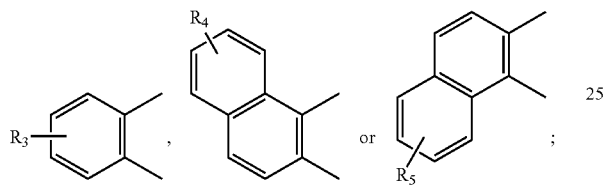

$R_3$, $R_4$ and $R_5$ are each independently selected from at least one of the following: H, halogen, cyano, hydroxyl, $C_{1-18}$alkyl, $C_{1-18}$alkylsulphonyl, sulphonyl and $C_{1-5}$alkylCOOR$_7$, provided that $R_3$ are not simultaneously sulphonyl when Y is —CH—CH=CH— and

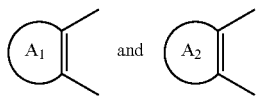

are simultaneously

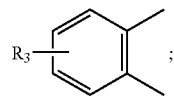

$R_7$ is H or $C_{1-6}$alkyl; and $Z^-$ is an anion;

wherein the compound of formula I is present in a concentration of from about 0.01 ppm to about 1000 ppm and configured to permit detection of erythroblasts and basophils; and (2) at least one surfactant selected from cationic surfactants and nonionic surfactants, wherein the cationic surfactant is selected from quaternary ammonium salt-type cationic surfactants having the following general formula II:

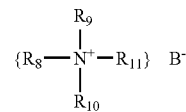

wherein $R_8$ is alkyl or alkenyl having 6 to 14 carbon atoms;

$R_9$ and $R_{10}$ are alkyl or alkenyl having 1 to 4 carbon atoms;

$R_{11}$ is alkyl or alkenyl having 1 to 4 carbon atoms, or benzyl; and

B is a halogen atom; and the nonionic suractant is selected from at least one of the following: octylphenylpolyoxyethylene ether, polyoxyethylene(10)cetyl ether, polyoxyethylene(23)cetyl ether, polyoxyethylene(25)cetyl ether and polyoxyethylene(30)cetyl ether;

wherein the at least one surfactant is present in a concentration of from about 50 mg/L to about 5000 mg/L and is configured to lyse erythrocytes.

* * * * *